United States Patent [19]

Wohlgemuth et al.

[11] Patent Number: 4,499,906

[45] Date of Patent: Feb. 19, 1985

[54] PERCUSSION INSTRUMENT

[75] Inventors: Jûergen Wohlgemuth, Darmstadt; Eugen Hohmann, Bensheim, both of Fed. Rep. of Germany

[73] Assignee: Siemens Aktiengesellschaft, Berlin & Munich, Fed. Rep. of Germany

[21] Appl. No.: 483,881

[22] Filed: Apr. 11, 1983

[30] Foreign Application Priority Data

Apr. 26, 1982 [DE] Fed. Rep. of Germany ....... 3215530

[51] Int. Cl.³ .............................................. A61B 5/00
[52] U.S. Cl. ................................... 128/776; 128/777; 73/82
[58] Field of Search ....................... 128/774, 776, 777; 73/82, 11, 12

[56] References Cited

U.S. PATENT DOCUMENTS

| 3,094,115 | 6/1963 | Polin | 128/776 X |
| 3,498,388 | 3/1970 | Jovis | 73/82 X |
| 3,653,373 | 4/1972 | Batterman | 128/776 X |
| 3,782,188 | 1/1974 | Koober et al. | 128/776 X |
| 4,192,321 | 3/1980 | Korber et al. | 128/776 |
| 4,195,512 | 4/1980 | Reid | 73/82 X |

FOREIGN PATENT DOCUMENTS

| 2733081 | 2/1979 | Fed. Rep. of Germany | 128/776 |
| 2853252 | 6/1980 | Fed. Rep. of Germany . | |
| 2617779 | 2/1982 | Fed. Rep. of Germany . | |

*Primary Examiner*—Edward M. Coven
*Attorney, Agent, or Firm*—Hill, Van Santen, Steadman & Simpson

[57] ABSTRACT

A percussion instrument suitable for use in dental practice for determining the degree of looseness of teeth has a movably seated ram which is accelerated to a defined velocity by an electromagnetic drive means and is subsequently moved toward a test subject (such as a tooth) in free flight. The electromagnetic means also controls return of the ram to a rest position. The ram is comprised of a non-magnetic section and a section of low magnetic retentivity passing through a magnetic coil. Control electronics supplies current pulses to the coil. The velocity of the ram is detected by a measuring and evaluation unit and is maintained at a constant value after a comparison of a rated value with the actual velocity value. The current feed to the coil is discontinued when the rated velocity is reached.

18 Claims, 8 Drawing Figures

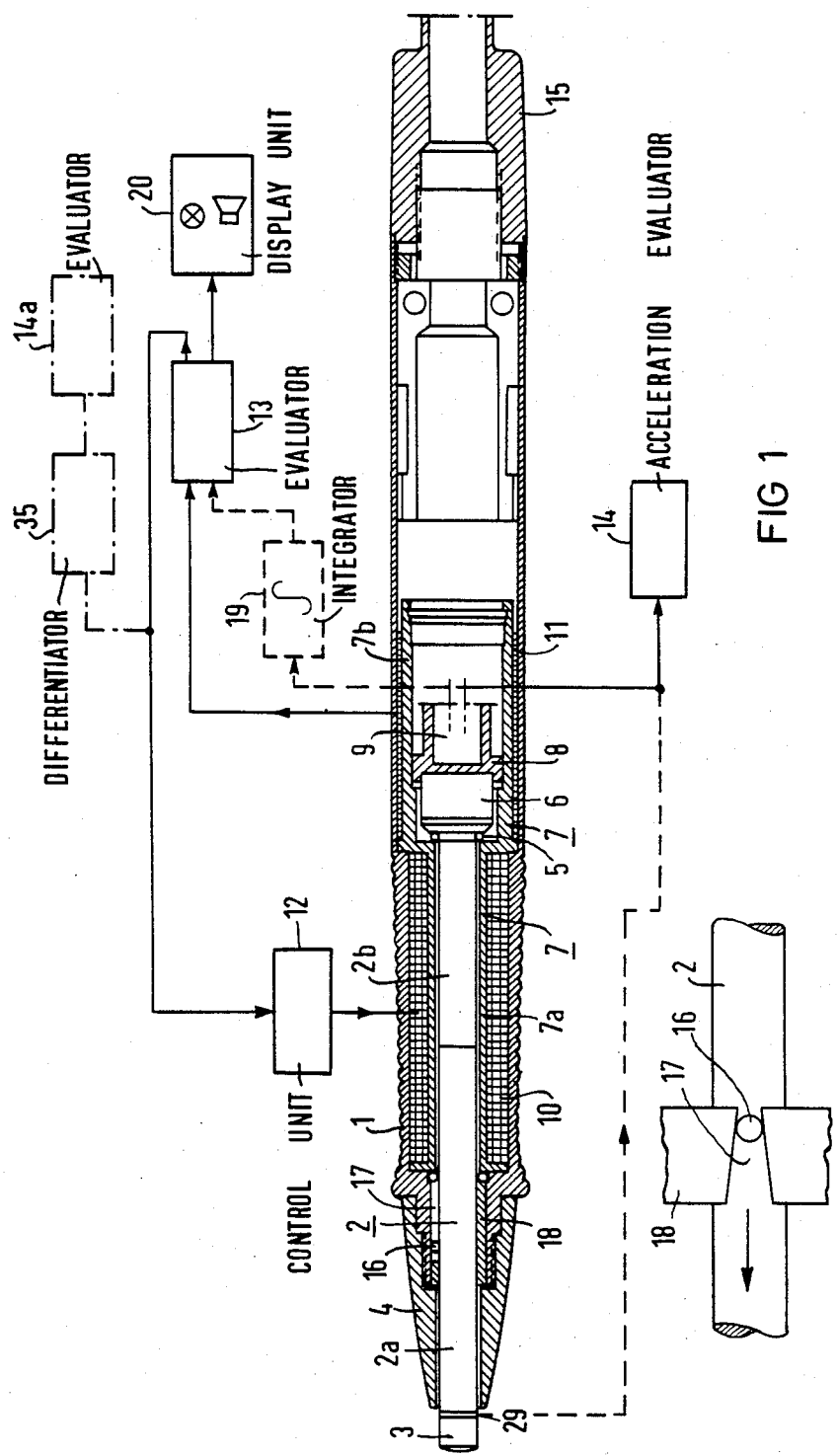

PERCUSSION INSTRUMENT

BACKGROUND OF THE INVENTION

1. Field of the Invention

The present invention relates to a percussion instrument of the type utilized in dental practice for determining the degree of looseness of teeth in the gum tissue- and in particular to such a percussion instrument having a ram which is accelerated from a rest position to a defined speed by the application of a force thereto and is moved toward a test subject such as a tooth in free flight with a constant velocity, and which returns to its initial position by the application of a magnetic field.

2. Description of the Prior Art

A percussion instrument having a displacably seated ram which is accelerated to a specific speed toward a test object by means of a spiral spring disposed in a front portion of the instrument containing the test head, and which is held in its initial position by means of a magnetic coil is disclosed in German OS No. 2,617,779. After complete relaxation of the spring, the ram separates from the spring and, conducted by means of bearings, proceeds in free flight toward the object to be tested with a theoretically constant speed. After impact against the test object, the ram is repelled in the direction toward its initial position by the reactive counter force arising as a result of the impact. The coil is subsequently supplied with a current pulse at the end of the return motion of the ram. The ram is returned to its initial position by the magnetic field generated thereby and the spring is again tensioned. An acceleration pickup connected to the ram by a flexurally slack cable detects a change in the ram velocity upon impact of the ram against the object. During the excursion and return motion, this change of velocity at the object can be evaluated for specific test and diagnostic purposes by means of an evaluation electronics unit connected to the acceleration pickup.

In dental practice, for example, for detecting tooth mobility, that is, the degree to which a tooth is loose, the time within which, after occurrence of the pulse by the ram, the tooth to be tested is subjected to an impact by the ram at a theoretically known velocity and the time within which the ram returns to its initial position is a measure of the degree of looseness of the tooth in the gum tissue.

In conventional devices of the type described above, the front portion of the instrument, from which the ram having a test head attached thereto emerges, is relatively large in diameter due to the spring arrangement. Working with such an instrument, particularly in dental practice, is thus rendered difficult. Another significant disadvantage associated with instruments of the type described above, is that when the instrument is applied to the test subject at an attitude deviating from the horizontal, the velocity of the ram is influenced by the accelerating force of gravity, which can result in falsification of the test results.

Another disadvantage of conventional percussion instruments is that the connecting lines attached to the acceleration pickup, and thus participating in the ram motion, can easily tear when the ram is twisted. The use of anti-twist devices connected to the ram in conventional percussion instruments result in undesired additional friction forces.

SUMMARY OF THE INVENTION

It is an object of the present invention to provide a percussion instrument for accelerating a ram at a defined velocity toward a test object and for measuring the reactive motion of the ram after impact with the test object having an ergonomic structure including a small diameter and a precisely definable ram velocity.

Another object of the present invention is to provide a percussion instrument of the type described above which ensures that the ram velocity at the end of the acceleration phase is constant even at an oblique position of the instrument, that is, uninfluenced by acceleration due to gravity.

The above objects are inventively achieved in a percussion instrument having a magnetic drive for both the forward motion of the ram as well as the return motion of the ram to its initial position. The ram utilized in combination with this magnetic drive has at least two adjacent ram sections consisting respectively of non-magnetic material and low magnetic retentive material. The drive system further includes at least one drive coil concentrically surrounding the ram into which the low magnetic retentive section of the ram enters up to approximately half the coil length when the ram is in its initial position. The percussion instrument further includes control electronics for supplying periodic current pulses to the drive coil and a measuring and evaluation means for identifying the ram velocity. The measuring and evaluation means includes a comparator circuit which undertakes a comparison of the actual value of ram velocity with a rated value. The drive means also includes a switch means for shutting off current supply to the coil when the rated velocity is reached.

The drive means may also consist of two drive coils, one for the forward motion of the ram and one for its return motion. The same function can be achieved, however, with a single drive coil in conjunction with a permanent magnetic body disposed at the end of the ram, the single drive coil being supplied with current pulses having periodically reversed polarity. The ram velocity can be measured by an acceleration pickup attached to the ram, the velocity being derived by means of a separate measuring coil or by means of an integrating stage. If an integrating stage is utilized, the measuring coil is not necessary.

A further embodiment of the invention includes one or more piezo-ceramic wafers of the type known to those skilled in the art which are utilized as the acceleration pickup but which are disposed at the front ram section containing the test head, or in the test head itself. In this embodiment the outlay for manufacturing the acceleration pickup is considerably reduced and the signal generation is more efficient. As a result of the different masses which influence the piezo-ceramic wafer is upon impact and upon the return motion, namely, a relatively large mass upon impact and a relatively small mass in comparison thereto upon return of the ram, useful signals which are higher by several powers than those produced by means of a conventional acceleration pickup disposed at the opposite end of the ram can be obtained.

The acceleration signals can also be obtained by means of a differentiating stage operating in conjunction with the measuring coil. This embodiment has the advantage that the ram is lighter as a result of eliminating the acceleration pickup, and no connecting cable is required.

The control electronics preferably supplies a current compensating the bearing friction in the free-flight phase of the ram such that a velocity drop is measured by suitable measuring means and is compensated for by a higher current.

In another embodiment of the invention which permits the instrument to be positioned at different angles relative to the horizontal without data falsification includes a digital limit selector in the control electronics for determining a maximum and minimum ram velocity in the freeflight phase taking the inclined attitude of the instrument relative to the horizontal into consideration. Signal generators activated by the digital limit selector provide an upward or downward transgression of the limiting values. Extreme oblique positions of the instrument, for example, deviating by more than ±10° from the horizontal, which would lead to a substantial change in the ram velocity in its free flight phase, can be displayed for the user for the purpose of undertaking a necessary correction of the instrument position.

BRIEF DESCRIPTION OF THE DRAWINGS

FIG. 1 is a sectional view of a percussion instrument constructed in accordance with the principles of the present invention including a schematic block diagram of control and evaluation circuitry for the instrument;

FIG. 2 is an enlarged detail of a portion of the instrument shown in FIG. 1 for twist-free seating of the ram;

FIG. 4b shows respective current/time and voltage/time diagrams for the drive and return current when the instrument is in the position shown in FIG. 4a;

FIG. 5 shows current/time and voltage/time diagrams for the instrument in the position shown in FIG. 5a;

DESCRIPTION OF THE PREFERRED EMBODIMENTS

Figure 3:
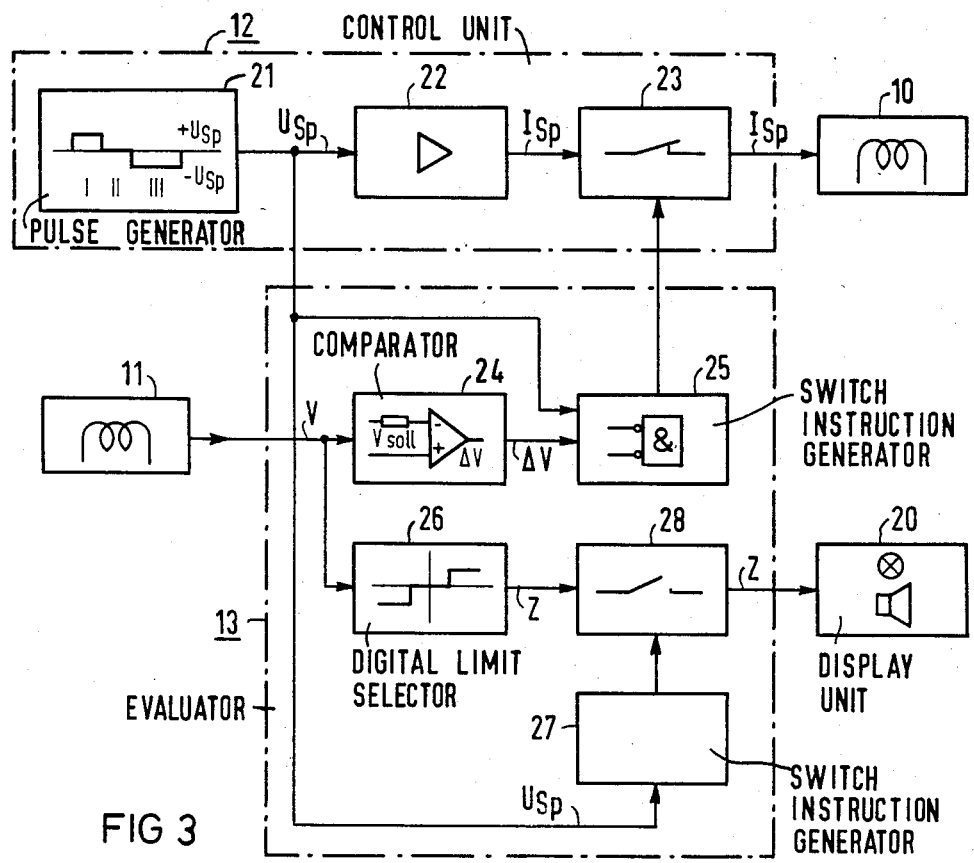
FIG. 3 is a block diagram of the control unit and evaluator shown in FIG. 1.

A percussion instrument constructed in accordance with the principles of the present invention together with associated control and measuring electronics are shown in FIG. 1. The instrument includes a housing 1, designed for hand-held use, having a ram 2 movably seated therein in substantially friction-free manner. The ram 2 includes a section 2a consisting of non-magnetic material such as, for example, aluminum, and a section 2b consisting of material of low magnetic retentivity. In the position shown in FIG. 1, the ram 2 is at a final position in which its front end, having a test head 3, projects from the conically tapering housing front end 4. An O-ring 5 serves as a detent means, the O-ring 5 pressing against a shoulder of a sleeve 7 disposed in the instrument housing 1, between the ram section 2b and a magnetic member 6 rigidly connected thereto. A flux conducting element 8 and an acceleration pickup 9 are rigidly connected to the magnetic member 6.

The sleeve 7 is of one-piece construction and consists of two sections 7a and 7b disposed concentrically relative to one another. A drive coil 10 is disposed around the sleeve section 7a and a measuring coil 11 is disposed around the sleeve section 7b. The drive coil 10 is connected by means of a cable to control electronics 12, the measuring coil 11 is connected to an evaluation means 13, and the acceleration pickup 9 is connected to an acceleration evaluator 14. The acceleration evaluator 14 receives the acceleration signals and processes those signals upon impact of the test head 3 against an object (for example, a tooth, to be tested). Although the connecting lines are schematically shown in the drawing for purposes of clarity as proceeding directly from the respective components, in reality the lines are conducted from a rear connection element 15 to a unit containing the control and evaluation electronics.

In order to protect the ram 2 against twisting, the ram 2 has a pin 16 at its front section 2a, the pin 16 extending at a right angle relative to the longitudinal ram axis. The pin 16 is conducted during a raw stroke in a dove-tail groove 17 of a ring 18 mounted in the housing section 4. This anti-twisting structure is shown in greater detail in FIG. 2. This type of anti-twisting structure is substantially friction-free.

The drive coil 10 is disposed such that the transition from the section 2a into the section 2b of the ram 2 occurs approximately at the center of the drive coil 10 in the illustrated front final position of the ram 2 shown in FIG. 1. As a result of the combination of the magnetic coil and the permanent magnet, the drive coil 10 may be utilized both for the forward and the return motion of the ram 2 by suitably reversing the polarity of the current pulses supplied to the drive coil 10.

The permanent magnet 6 may be comprised, for example, of cobalt-samarium in which case an iron structure around the coil can be eliminated because of the high magnetic energy product and high conductive field strength of this type of magnetic material. The structural diameter of the instrument can thus be maintained very small, particularly at the front end of the instrument. The magnetic element 6 also promotes intensification of the forward motion of the ram.

The flux conducting element 8 is for the purpose of directing magnetic flux through the measuring coil 11 and to concentrate that flux so that the voltage induced in the measuring coil 11 by the moving magnet can be suitably employed as an output which serves as a precise indicator of the ram velocity.

A display unit 20, which may be acoustic or optical, processes the signals obtained from the measuring coil 11 and evaluated in the evaluation means 13 for display of the final signal. Upon the occurrence of an inadmissable oblique positioning of the instrument, an optical and/or acoustical indication thereof is supplied, as described in greater detail below.

The manner of operation of the control unit and the measuring and evaluation means 13 is explained in greater detail on the basis of the block diagram shown in FIG. 3. The control unit 12 contains a pulse generator 21 for supplying a positive signal ($+U_{SP}$) to the drive coil 10 for forward motion of the ram and supplies a negative signal ($-U_{SP}$) for the return motion. Those respective phases of the ram motion are designated as phase I and phase III. In between those phases is a free flight phase II during which the ram 2 is propelled forward in the absence of any externally applied force. An amplifier stage 22 is connected to the output of the pulse generator 21 which supplies a current $I_{SP}$ through a switch 23 for driving the coil 10. The switch 23 is controlled by a signal from the evaluator 13 and interrupts supply of drive current to the coil 10 during forward motion (phase 1 of the pulse generator 21) when the ram 2 reaches a rated velocity. For that purpose, the velocity signal obtained from the measuring coil 11 is compared with a prescribed rated value $V_{soll}$ in a comparator 24. The result of the comparison ($\Delta V$) is supplied to a switch instruction generator 25 (which may be an AND gate) together with the output from the pulse generator 21. The switch instruction generator 25 opens the switch 23 when the velocity difference $\Delta V$ is zero and when the voltage output of the pulse generator 21 is greater than zero.

The velocity signal V from the measuring coil 11 is simultaneously supplied to a digital limit selector 26 which measures transgression of permissible deviations from the rated velocity during the free flight phase of the ram (phase II) and optically or acoustically informs the user of the instrument of an impermissible oblique attitude of the instrument by supplying a signal Z to the display unit 20. For this purpose, another switch instruction generator 27 is provided which controls a switch 28 which connects the signal Z to the display unit 20 when the ram 2 is in free flight, that is, when $U_{sp}=0$.

In addition to the acceleration provided by the drive means, the ram 2, given an oblique attitude of the instrument, is normally also accelerated by the force of gravity $F_E$ according to the relationship $F_E = m_{ST} \cdot g \cdot \sin \alpha$, where $m_{ST}$ is the mass of the ram 2, g is the gravitational acceleration constant, and $\alpha$ is the angle of the oblique attitude.

Figure 4A:
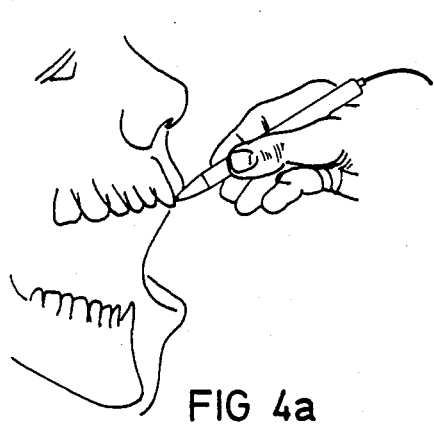
FIG. 4a shows an upwardly oblique position of the instrument in use.
Figure 5A:
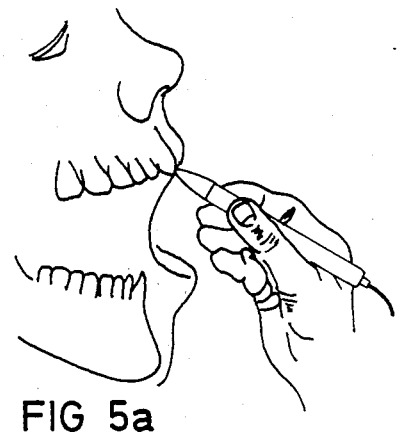
FIG. 5a shows another oblique position of the instrument in use.
Figure 4:
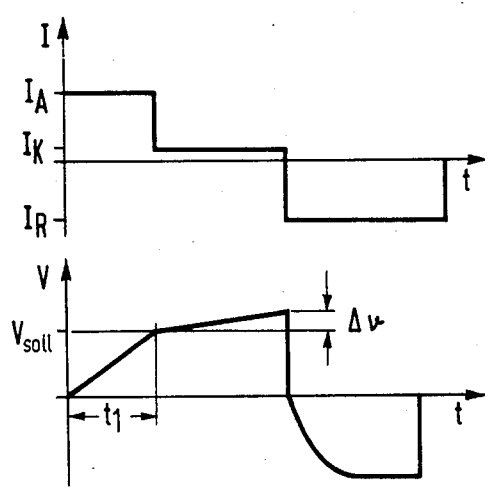
Figure 5:
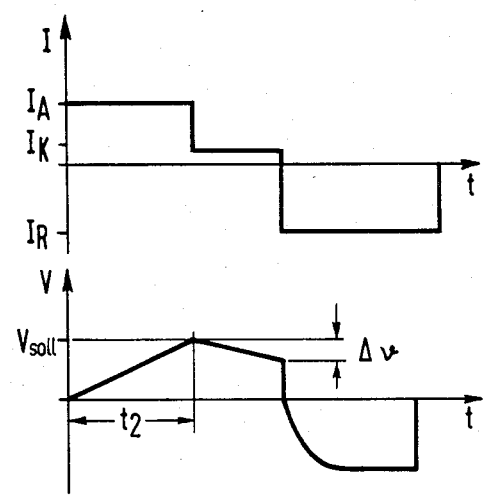

In order to avoid an impermissibly large velocity error, the velocity of the ram 2, as explained above, is measured and compared to the rated velocity. The drive pulse is disconnected precisely at the moment at which the ram reaches its rated velocity. Depending upon the size of the oblique attitude angle $\alpha$, the drive pulses may be of varying lengths. Given a large oblique attitude of the instrument, the rated velocity is reached earlier than in the case of a less greatly inclined instrument. Accordingly, the chronological duration of the drive pulse is higher given a less greatly inclined instrument than given a large oblique inclination. The ram velocity will also decelerate, or increase, during the free flight phase depending upon the oblique attitude of the instrument. Two different oblique positions of the instrument, as applied to a patient, are respectively shown in FIGS. 4a and 5a and the associated current and voltage paths with respect to time are shown for those positions in FIG. 4 and FIG. 5.

Deviation of the velocity V from the rated velocity $V_{soll}$ is determined by the evaluator 13 shown in FIG. 3. When a fixed admissible limiting value is transgressed during the free flight phase II, this inadmissible positioning is identified optically or acoustically as described above. A slight drop in velocity during the free flight phase II as a result of bearing friction is compensated by a small compensation current $I_K$.

A further embodiment of the instrument is also indicated in FIG. 1 in dashed lines and dashed components wherein only one drive coil is provided and control of the ram return is undertaken by means of reversing the polarity of the magnetic flux in combination with the magnetic element 6.

Figure 6:
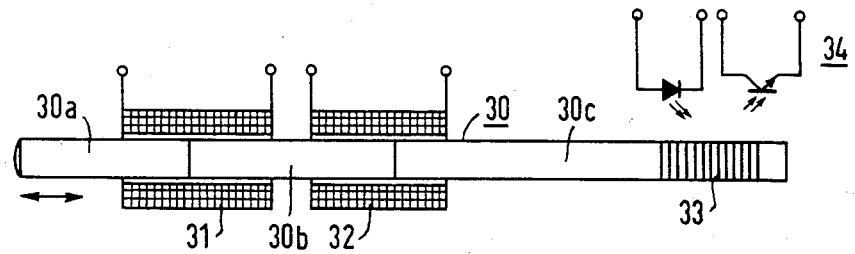
FIG. 6 is a schematic illustration of a further embodiment of the invention.

The ram may also be driven by means of a double coil arrangement as shown in FIG. 6. In this embodiment, the ram 30 consists of two sections 30a and 30c each consisting of non-magnetic material, and an intervening ram section 30b consisting of soft iron. A drive coil 31 surrounds the transition region between the section 30a and 30b, and a second drive coil 32 surrounds the transition region between the sections 30b and 30c. The ram 30 is further provided with a marked section 33 which cooperates with a reflection light transmitter/receiver 34 disposed in the instrument housing. The light transmitter/receiver 34 optically detects the velocity of the ram 30 by means of the varying reflections generated by the marked section 33. Evaluation of the velocity and control of the coils is undertaken in a manner analogous to that discussed above in connection with the embodiment of FIGS. 1 and 3.

In another embodiment of the invention, the acceleration signals are not obtained by means of an acceleration pickup but are instead derived by means of a differentiation stage 35 shown in dot-dash lines in FIG. 1. The acceleration b is determined by the relationship $b = dv/dt$. The differentiation stage 35 is connected to the evaluator 13 and converts the velocity signals obtained by means of the measuring coil 11 into acceleration signals, which are then processed further in a known manner in another evaluator 14a.

Another embodiment is indicated with dashed lines in FIG. 1 wherein the velocity signal v is derived by the acceleration pickup 9 by means of an integrator 19 according to the relationship $v = \int b \, dt$ (where b is again the acceleration). In this embodiment, the measuring coil 11 can be eliminated. The velocity signals are further processed in the manner described above in the evaluator 13.

A particularly simple and economic structure for the acceleration pickup means (instead of the conventional acceleration pickup 9) is also shown in FIG. 1. In this embodiment, the acceleration pickup is not disposed at the rear of the ram but is instead disposed at the front ram section, preferably behind the test head 3. The acceleration pickup is in the form of one or more lamina 29 of piezo-ceramic material which subdivides the ram into different mass components. Upon impact of the ram (that is, of the test head 3) against the object to be tested, substantially the entire ram mass influences the piezo-ceramic lamina 29 as a force, with the consequence that a relatively high useful signal is obtained therefrom. In contrast thereto, only a slight mass is effective against the lamina 29 upon return of the ram to its initial position. Upon impact of the ram against the limitations provided in the housing 1 which define the initial position of the ram 2, the only mass effecting the lamina 29 is that of the test head 3, causing the generation of a very small noise signal.

Although modifications and changes may be suggested by those skilled in the art, it is the intention of the inventors to embody within the patent warranted hereon all changes and modifications as reasonably and properly come within the scope of their contribution to the art.

We claim as our invention:
1. A percussion instrument comprising:
a housing;
a ram displacably seated in said housing consisting of at least a section of non-magnetic material and a section of low magnetic retentive material;
a drive means for accelerating said ram from an initial position to free flight at a constant velocity toward an object to be tested by the reactive rebound of said ram there against and for returning said ram to said initial position, said drive means including at least one drive coil surrounding a portion of said ram and into which said low magnetic retentive section of said ram extends up to approximately one-half of the length of said coil when said ram is in said initial position;

a control means connected through a switch to said drive means for supplying periodic current pulses to said drive coil; and an evaluator means including a measuring means for measuring the velocity of said ram, a comparator for comparing the actual value of said ram with a rated velocity value, and a switch control means for interrupting the connection between said drive means and said control means when said actual velocity equals said rated velocity during acceleration of said ram.

2. A percussion instrument as claimed in claim 1 wherein said drive means includes a single drive coil and further comprising a permanent magnetic element disposed at a free end of said low magnetic retentive section of said ram, and wherein said control means further includes a means or periodically reversing the polarity of said current pulses supplied to said drive coil.

3. A percussion instrument as claimed in claim 2 wherein said ram section of non-magnetic material is a front section of said ram closest to said test object, and wherein said front section further comprises a test head.

4. A percussion instrument as claimed in claim 2 wherein said measuring means is a measuring coil mounted in said housing and surrounding said permanent magnetic element.

5. A percussion instrument as claimed in claim 4 further comprising a one-piece coil carrier having stepped diameters mounted in said housing and having said drive coil and said measuring coil mounted thereon.

6. A percussion instrument as claimed in claim 2 wherein said permanent magnetic element consists of cobalt-samarium.

7. A percussion instrument as claimed in claim 2 further comprising an acceleration pickup mounted on said ram for detecting acceleration of said ram and being connected to said evaluator means, and further comprising a magnetic flux guide element disposed between said acceleration pickup and said permanent magnetic element.

8. A percussion instrument as claimed in claim 1 further comprising an acceleration pickup mounted on said ram for detecting acceleration of said ram and being connected to said evaluator means and further comprising an integration stage interconnected between said acceleration pickup and said evaluator means for integrating the acceleration value of said ram for deriving the velocity of said ram.

9. A percussion instrument as claimed in claim 4 further comprising a differentiator connected to said evaluator means for differentiating the signal from said measuring coil for converting velocity signals from said measuring coil into acceleration signals, and further comprising a means for evaluating said acceleration signals connected to said differentiator.

10. A percussion instrument as claimed in claim 1 wherein said ram consists of two sections of non-magnetic material and an intervening section of low magnetic retentive material, and wherein said drive means includes two drive coils for respectively controlling forward and return motion of said ram.

11. A percussion instrument as claimed in claim 1 further comprising a marked section on said ram and a light transmitter-receiver mounted in said instrument housing for directing light toward said marked section and monitoring the reflection therefrom for measuring the velocity of said ram.

12. A percussion instrument as claimed in claim 1 further comprising a pin carried on said ram extending perpendicularly to a longitudinal axis of said ram and further comprising a ring mounted at an end of said housing closest to said test object, said ring surrounding said ram and having a dove-tail groove therein for receiving said pin for preventing twisting of said ram.

13. A percussion instrument as claimed in claim 1 wherein said control means supplies a compensating current to said drive means while said ram is in free flight for compensating for friction experienced by said ram, said compensating current being generated in an amount for overcoming a drop in ram velocity measured by said measuring means during free flight of said ram.

14. A percussion instrument as claimed in claim 1 wherein said control means further includes a digital limit selector for setting a maximum and a minimum ram velocity for said ram in free flight, said digital limit selector monitoring the inclined attitude of said instrument relative to the horizontal, and said percussion instrument further comprising a signal generator connected to said digital limit selector for providing a signal to a user indicating the transgression of said ram velocity above said maximum velocity or below said minimum velocity in free flight of said ram.

15. A percussion instrument as claimed in claim 14 wherein said signal generator is an optical display means.

16. A percussion instrument as claimed in claim 14 wherein said signal generator is an acoustical signal generator.

17. A percussion instrument as claimed in claim 1 further comprising a test head carried on a front of said ram closest to said test object, said test head including an acceleration pickup for detecting the acceleration of said ram.

18. A percussion instrument as claimed in claim 17 wherein said acceleration pickup comprises one or more piezo-electric lamina disposed in a plane at a right angle relative to a longitudinal axis of said ram.

* * * * *